United States Patent
Nakamura (10) Patent No.: US 6,464,648 B1
(45) Date of Patent: Oct. 15, 2002

(54) BIOPSY DEVICE AND REMOTE CONTROL DEVICE THEREFOR

(75) Inventor: Katsushige Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 09/200,352

(22) Filed: Nov. 9, 1998

(30) Foreign Application Priority Data

Dec. 26, 1997 (JP) .............................................. 9-361458

(51) Int. Cl.⁷ .............................................. A61B 10/00
(52) U.S. Cl. ........................ 600/567; 600/564; 606/167
(58) Field of Search ............................... 600/562, 564, 600/567; 606/130, 167, 170, 172, 181, 182

(56) References Cited

U.S. PATENT DOCUMENTS

| | | | | |
|---|---|---|---|---|
| 4,699,154 A | | 10/1987 | Lindgren | 128/754 |
| 4,953,558 A | * | 9/1990 | Akerfeldt | 600/564 |
| 5,078,140 A | * | 1/1992 | Kwoh | 600/417 |
| 5,161,542 A | | 11/1992 | Palestrant | 600/567 |
| 5,507,298 A | * | 4/1996 | Schramm et al. | 600/567 |
| 5,546,957 A | * | 8/1996 | Heske | 600/567 |
| 5,575,798 A | * | 11/1996 | Koutrouvelis | 606/130 |
| 5,645,556 A | | 7/1997 | Yoon | 606/185 |
| 5,647,373 A | * | 7/1997 | Paltieli | 600/567 |
| 5,782,775 A | * | 7/1998 | Milliman et al. | 600/567 |
| 5,842,999 A | * | 12/1998 | Pruitt et al. | 600/562 |
| 5,957,933 A | * | 9/1999 | Yanof et al. | 606/130 |

* cited by examiner

*Primary Examiner*—Kevin Shaver
*Assistant Examiner*—Charles Marmor, II
(74) *Attorney, Agent, or Firm*—Jordan and Hamburg LLP (57) ABSTRACT

A biopsy device, including:

a housing having a shape of a container, the housing having an opening on a first side thereof, a cannula, a biopsy needle, wherein the biopsy needle is inserted into the cannula, wherein the cannula and the biopsy needle are received within the housing such that the cannula and the biopsy needle are vertically movable within the housing, a first hook, wherein the first hook is in engagement with the biopsy needle; a first spring, wherein the first spring urges the biopsy needle downward, second hook, wherein the second hook is in engagement with the cannula; and a second spring, wherein the second spring urges the cannula downward.

The first hook and the second hook are located within the housing. The first hook releases the biopsy needle and the second hook releases the cannula causing the biopsy needle to protrude downward prior to the cannula protruding downward. The biopsy needle is spaced apart from the first spring and the cannula is spaced apart from the second spring. The biopsy needle and the cannula can be displayed on an image screen without overlapping the first spring and the second spring.

27 Claims, 12 Drawing Sheets

BIOPSY DEVICE AND REMOTE CONTROL DEVICE THEREFOR

BACKGROUND OF THE INVENTION

1. Field of the Invention

This invention relates to a biopsy device and a remote control device therefor for use in biopsy performed under the guidance of CT or MRI (hereinafter referred to as "CT or the like").

2. Prior Art

A biopsy is carried out under the guidance of CT or the like is a method which has wide application in the field of clinical medicine, and the effectiveness and safety of the methods are approved. Further, recent progress in the technology of CT apparatuses has made it possible to reconstruct an image obtained by CT at a very high speed, whereby the image has come to be displayed in real time. That is, it has become possible to show a metal biopsy needle and a metal cannula having the biopsy needle inserted therethrough in the image obtained by CT and position a distal end of the biopsy needle to a desired site (tumor or the like) accurately.

However, according to the above conventional techniques, biopsy devices used under the guidance of CT or the like are those which have been conventionally used for biopsy but not designed assuming that they are displayed in the image screen of an apparatus of the CT and the like. Hence, at locations close to a biopsy needle and a cannula which are objects to be displayed on the screen, there are provided metal springs for urging the needle and the cannula to be protruded in a downwardly manner so that the metal springs can be displayed on the screen in a manner overlapping the needle and/or cannula, which can make it difficult to confirm the position of the biopsy needle on the screen.

Further, when the biopsy is carried out with the image obtained by the CT or the like being displayed in real time, the operator has to hold the biopsy device with his/her hand in a radiation area, which compels the operator to be exposed to doses of radiation whenever a biopsy is carried out.

SUMMARY OF THE INVENTION

The invention has been made noting the above conventional techniques. The invention provides a biopsy device which enables the positions of a biopsy needle and a cannula to be clearly recognized on the image screen, and a remote control device for a biopsy device, which prevents the operator from being exposed to doses of radiation.

In a preferred embodiment of the present invention, there is provided a biopsy device including a nonmetal housing having a shape of a container. The housing is provided with an opening on one side thereof having associated therewith a metal cannula, and a metal biopsy needle for being inserted into the metal cannula, with the cannula and the needle being received within the housing with respective distal ends thereof protruding downward in a manner such that the metal cannula and the metal biopsy needle are vertically movable within the housing. Within the housing on another side thereof with respect to the biopsy needle and the cannula, there are provided a first hook in engagement with the biopsy needle and urging the biopsy needle downward by a metal spring, and a second hook in engagement with the cannula and urging the cannula downward by a metal spring. The first and second hooks are caused to release the biopsy needle and the cannula, respectively, thereby causing the biopsy needle to protrude downward prior to protrusion of the cannula with a slight time lag. The biopsy needle and the cannula are positively spaced from the respective metal springs of the first hook and the second hook by a predetermined distance in a direction perpendicular to a plane of radiation.

In a preferred embodiment of the present invention, the biopsy needle and the cannula are positively spaced from the respective metal springs of the first hook and the second hook by a predetermined distance in the direction perpendicular to the plane of radiation. Therefore, the biopsy needle and the cannula are prevented from being displayed on an image screen in a manner overlapping the springs, whereby it is possible to securely recognize positions of the biopsy needle and the like.

In another preferred embodiment of the present invention, the biopsy device includes a first stopper and a second stopper arranged on the other side of the first hook and the second hook, for engagement with the first hook and the second hook, respectively, to thereby inhibit the first hook and the second hook from moving downward, and a lock mechanism formed between the first stopper and the housing, the first stopper being permitted to move downward together with the first hook by unlocking the lock mechanism, the first stopper abutting the second stopper when the first stopper has moved downward over a predetermined distance to thereby disengage the second stopper from the second hook.

In another preferred embodiment of the present invention, the first stopper is permitted to move downward together with the first hook by unlocking the lock mechanism formed between the first stopper and the housing, and the first stopper abuts the second stopper when the first stopper has moved downward over a predetermined distance to thereby disengage the second stopper from the second hook. Therefore, it is possible to cause the biopsy needle to protrude downward prior to protrusion of the cannula with a slight time lag.

In another preferred embodiment, the housing has a linear groove or a linear ridge formed on a side thereof at a location aligned with the biopsy needle and the cannula, for causing the biopsy needle and the cannula to be aligned with the plane of radiation.

The aligning of the linear groove or linear ridge, with the plane of radiation, allows the biopsy needle and the cannula to be aligned with the plane of radiation.

In another preferred embodiment, a biopsy device is held at a distal end of an articulated arm via a fine-adjustment mechanism and the fine-adjustment mechanism and a lock mechanism of the biopsy device can be mechanically operated via a flexible transmission means.

The biopsy device is not held directly by hand but held on the distal end of the articulated arm, which prevents the operator from being exposed to doses of radiation. Further, it is possible for the operator remote from the biopsy device to operate the fine-adjustment mechanism for finely adjusting the position of the biopsy device and the lock mechanism of the biopsy device by the flexible transmission means. Furthermore, the above operation is executed mechanically, not electrically. Therefore, no electrical noise is generated.

The present invention can be used in conjunction with a remote control device. A biopsy device is held via a fine-adjustment mechanism at a distal end of a holder attachable to an operator's arm; and a fine-adjustment mechanism and a lock mechanism of the biopsy device can be mechanically operated via flexible transmission means.

In another preferred embodiment, the biopsy device is not held directly by hand but held on a distal end of the holder that is attachable to the operator's arm, which prevents the operator from being exposed to doses of radiation. Further, a flexible transmission means can operate the fine-adjustment mechanism for finely adjusting the position of the biopsy device and the lock mechanism of the apparatus In another preferred embodiment, the remote control device can hold an ethanol local injection device instead of the biopsy device.

The ethanol local injection device, instead of the biopsy, being held on a distal end of the remote control device, can effect ethanol local injection treatment under the guidance of the CT or the like.

The invention is not particularly limited to the above description, but the above and other objects, features, and advantages of the invention will become more apparent from the following detailed description taken in conjunction with the accompanying drawings. It is to be understood that various changes and modifications may be made thereto without departing from the spirit and scope thereof.

DETAILED DESCRIPTION OF THE PREFERRED EMBODIMENTS

The invention will now be described in detail with reference to drawings showing preferred embodiments thereof The following description will be made assuming that A represents a front side (one side) of each embodiment of the invention, B a rear side (another side) thereof, C a right-hand side thereof and D a left-hand side thereof.

FIGS. 1 to 9 show a biopsy device 1 according to a first embodiment of the invention. The first embodiment will describe a structure of the biopsy device 1. Reference numeral 2 designates a housing made of resin, which has a shape of a container having an opening on a front side thereof The opening of the housing 2 has a groove 3 formed vertically in each inner surface of the opposite lateral side walls so as to be opposed to each other. Further, around the opening of the housing 2, there are formed linear grooves 4 in a manner aligned with a plane of radiation R for use in CT or the like (linear ridges may be formed instead of the linear grooves 4). The housing has a protruding portion 5 on each opposite lateral side wall at a location close to the front side. Each protruding portion has the same length as the lower half of the housing 2.

Figure 1:
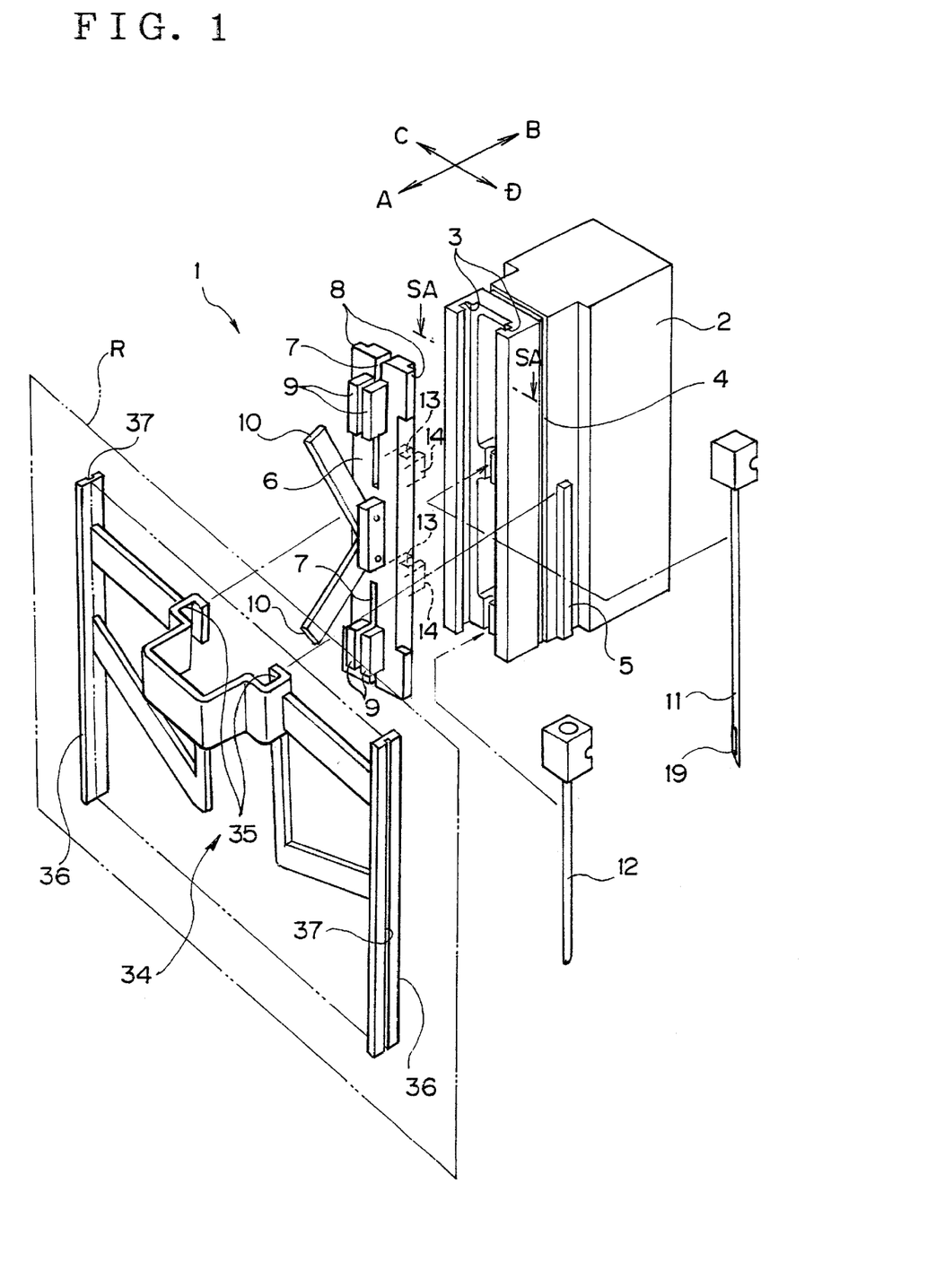
FIG. 1 is an exploded perspective view of a biopsy device according to a first embodiment of the present invention.
Figure 2:
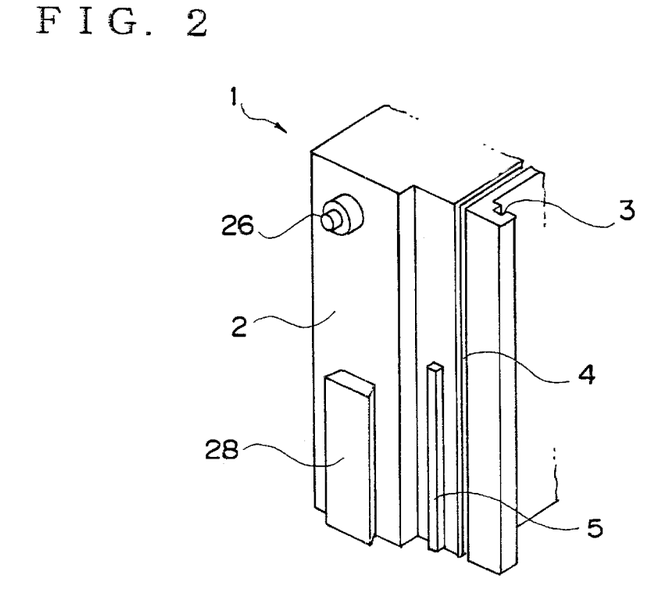
FIG. 2 is a perspective view of a right-hand side of the biopsy device.
Figure 3:
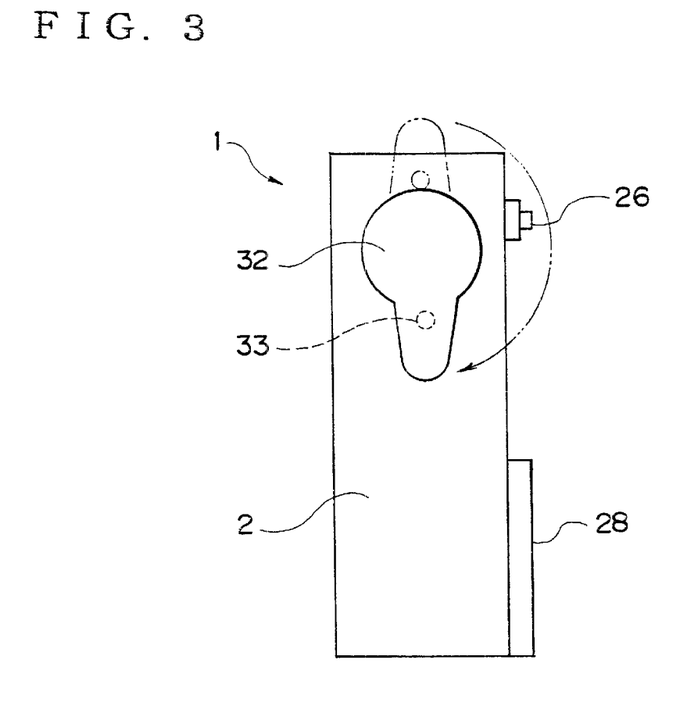
FIG. 3 is a rear end view of a housing of the biopsy device.

The opening of the housing 2 is closed by a lid 6. The lid 6 has an upper end and a lower end thereof divided into two portions by respective slits 7. On each side of the upper end of the lid 6 is formed a projection 8 for engagement with a corresponding one of the grooves 3. Further, each of the upper and lower ends of the lid 6 is formed with a pair of projecting pieces 9 opposed to each other across the slit 7. Levers 10 are pivotally supported on a central portion of the lid 6, for being fitted between the respective upper and lower pairs of the projecting pieces 9 to increase the gaps therebetween.

The lid 6 has a back formed with an upper holder 14 and a lower holder 14 each having a groove 13 for holding therein a biopsy needle 11 and a cannula 12, both described hereinafter. The groove 13 of each holder 14 is required to have a width corresponding to the thickness of the cannula 12 having the biopsy needle 11 inserted therein so as to be held by the holders 14, and the vertical stroke length of the biopsy needle 11 and that of the cannula 12 are determined according to a vertical distance between the holders 14. Therefore, a plurality of lids 6 are provided which have grooves 13 different in width and holders 14 different in vertical distance therebetween for selection of the optimal lid therefrom.

The housing 2 accommodates a first hook 15 at an upper location and a second hook 16 at a lower location. The first hook 15 and the second hook 16 are urged downward by a first metal spring 17 and a second metal spring 18, respectively.

The first hook 15 and the second hook 16 are engaged with respective upper portions of the biopsy needle 11 and the cannula 12. The needle 11 and cannula 12 have a metal distal end. The distal end of the biopsy needle 11 is formed with a pocket 19 for collecting a sample tissue and held in a state inserted in the distal end of the cannula 12. The respective distal ends of the biopsy needle 11 and cannula 12 are transversely aligned with the above linear grooves 4. The first metal spring 17 and the second metal spring 18 are spaced from the distal end of the cannula 12 by a predetermined distance L (see FIG. 6) of approximately 10 mm in a direction perpendicular to the plane of radiation R (transversely).

In the back of the first hook 15 and the second hook 16, there are arranged a first stopper 20 and a second stopper 21 for engaging with a lower end of the first hook 15 and that of the second hook 16, respectively, to thereby stop the downward movement of the stoppers. The first stopper 20 is arranged in a vertically slidable manner, whereas the second stopper 21 is pivotally supported on an axis extending through a lower end thereof and urged by a spring 22 in a direction of engaging with the second hook 16. The first stopper 20 has a lower end formed with protruding pieces 23 for engagement with the lower end of the second hook 16 (see FIG. 4).

Figure 4:
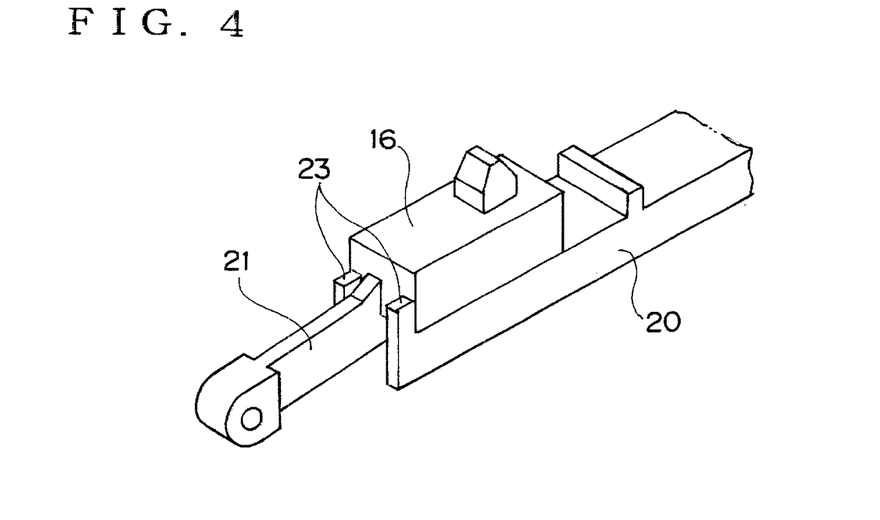
FIG. 4 is a perspective view of a first stopper and a second stopper of the biopsy device according to the first embodiment.
Figure 5:
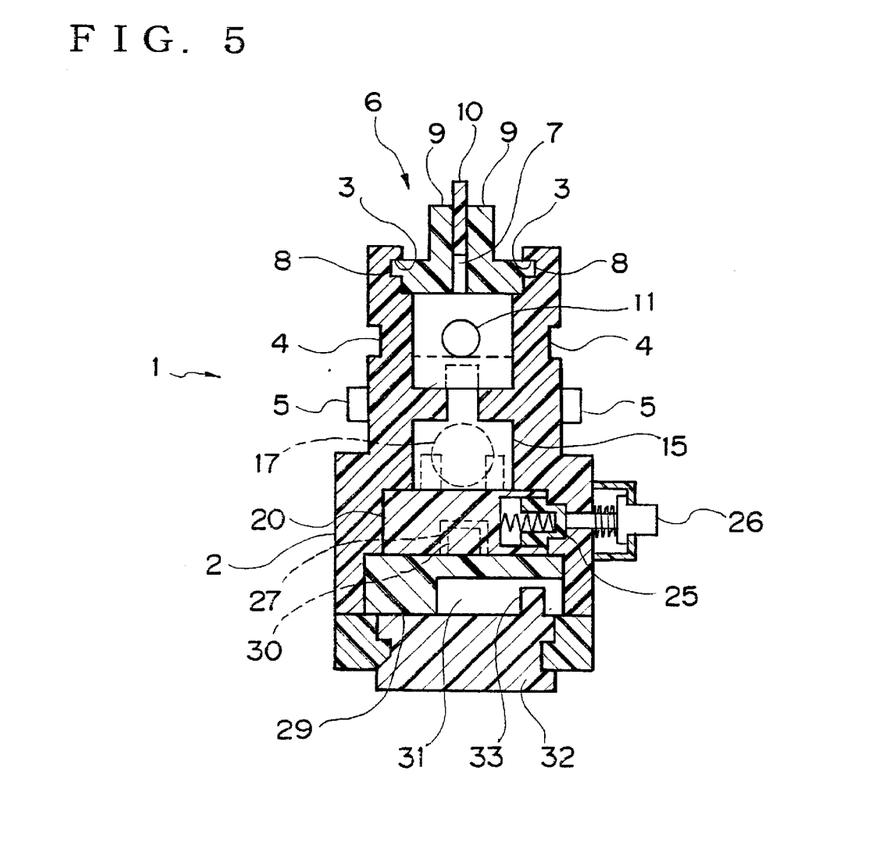
FIG. 5 is a cross-sectional view taken along a line SA—SA of FIG. 1.
Figure 6:
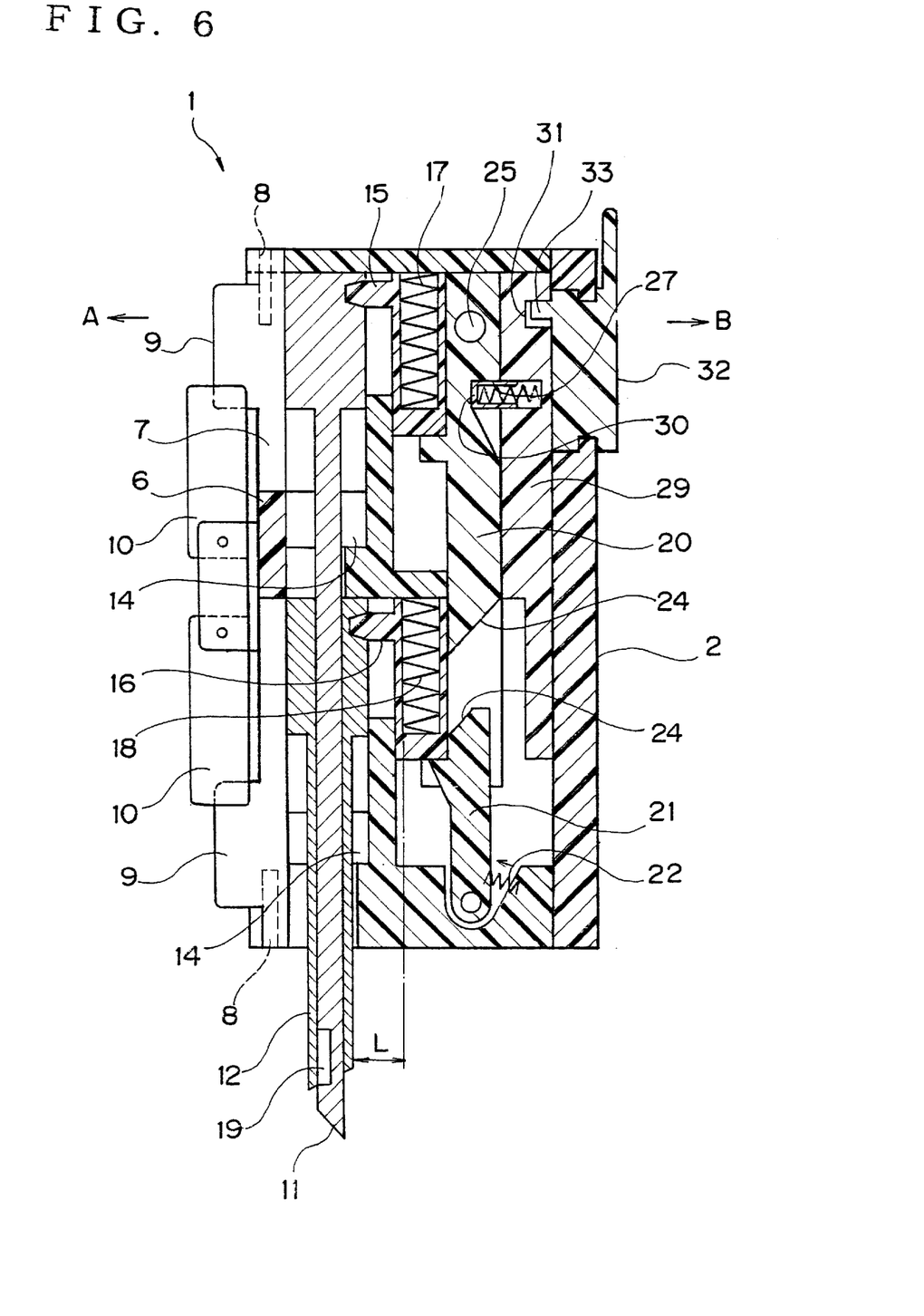
FIG. 6 is a cross-sectional view showing the biopsy device in a state in which a handle has not been turned yet.

The first stopper 20 and the second stopper 21 are vertically spaced from each other by a predetermined distance. The lower end of the first stopper 20 and an upper end of the second stopper 21 are opposed to each other and are formed with sloped surfaces 24 for pivotally moving the upper end of the second stopper 21 rearward against the urging force of the spring 22 when the lower end of the first stopper 20 and the upper end of the second stopper 21 are engaged with each other.

On a side of the first stopper 20 is arranged a lock mechanism 25 which is engaged with an inner surface of the housing 2 by the urging force of a spring to thereby prevent the first stopper 20 from moving downward. On a right side of the lock mechanism 25 is provided a start button 26 for pushing the lock mechanism 25 in a direction of disengagement from the inner surface of the housing 2. The start button 26 is normally urged in a direction of inhibiting the pushing of the lock mechanism 25. The first stopper 20 is formed at a rear side thereof with a latch recess 27 which has a sloped lower wall and a flat top wall. Further, the housing 2 is formed with a mounting block 28 at a right side surface thereof under the start button 26. The mounting block 28 has a shape corresponding in cross-section to the shape of a dovetail groove. It should be noted that the mounting block 28 is not used in the first embodiment but used in a second embodiment described hereinafter.

A slider 29 is provided in the back of the first stopper 20 in a vertically movable manner. The slider 29 has a latch 30 formed on a front side thereof for engagement with the latch recess 27 arranged on the rear side of the first stopper 20, the latch 30 being urged in an engaging direction. The slider 29 has a rear-side surface formed with a groove 31 which extends rightward from a central portion thereof A projection 33 of a handle 32 rotatably arranged on a rear wall of the housing 2 is engaged with the groove 31.

Further, reference numeral 34 designates a jig for positioning the housing 2. At a central portion of the jig 34, grooves 35 for engaging with the protruding portions 5 are formed in a manner opposed to each other. Right-hand and left-hand holding pieces 36 of the jig are each formed with a linear groove 37 for aligning the jig 34 with the plane of radiation R.

Next, the operation of the biopsy device 1 will be described.

First, the handle 32 on the rear wall of the housing 2 is rotated through 180 degrees to set the device 1. Then, the biopsy needle 11 and the cannula 12 are set within the housing 2 such that the biopsy needle 11 engages the first hook 15 and the cannula 12 engages the second hook 16. When the biopsy needle 11 and the cannula 12 are in the housing 2, the biopsy needle 11 extends through the cannula 12.

Next, the upper and lower projecting pieces 9 of the lid 6 are made closer by holding them manually to put the right-hand and left-hand projections 8 in the grooves 3 formed inside the opening of the housing 2. When the projecting pieces 9 are released after fitting the projections 8 within the grooves 3, the projections 8 are engaged with the grooves 3 whereby the lid 6 is mounted in the opening of the housing 2. Further, by fitting the levers 10 between the projecting pieces 9, the projections 8 are more firmly engaged with the grooves 3 to reliably close the opening of the housing 2 by the lid 6.

Then, the grooves 35 of the jig 34 are fitted onto the protruding portions 5 of the housing 2 from above. In this embodiment, since the protruding portions 5 on the opposite lateral side walls of the housing 2 have the same length as the lower half of the housing 2, there is no need to lift the jig 34 above the housing 2, so that there is no fear of the jig 34 hitting component parts of the device for the CT or the like, not shown, located above the housing 2.

With the jig 34 mounted on the housing 2, the linear grooves 37 of the jig 34 are made aligned with the plane of radiation R, for positioning the grooves. Although the radiation per se is invisible, illuminating light is emitted along with the radiation and hence by aligning the linear grooves 37 of the jig 34 with the illuminating light, the linear grooves 37 can be properly positioned. Through this positioning operation by using the jig 34, the housing 2 can be properly positioned with respect to the plane of radiation R. Since the plane of radiation R is aligned with the linear grooves 37 of the holding pieces 36 located away from each other in rightward and leftward directions with a large distance therebetween, the housing 2 can be positioned with high accuracy. After positioning the housing 2, the jig 34 is removed. After the jig 34 is removed, even if the housing 2 is displaced from its proper position, the linear grooves 4 formed in the housing 2 allows the position of the housing 2 corrected by aligning the linear grooves 4 with the plane of radiation R.

By aligning the linear grooves 4 of the housing 2 with the plane of radiation R, it is possible to display the biopsy needle 11 and the cannula 12 on the image screen of the CT or the like in real time. After displaying the biopsy needle 11 and the cannula 12 on the image screen, the position and orientation of the biopsy needle 11 is finely adjusted to a target site (tumor or the like) within a range of the width of the radiation R (approximately 5 mm). The biopsy needle 11 and the cannula 12 displayed on the screen are spaced from the first metal spring 17 and the second metal spring 18 by the predetermined distance L in the direction perpendicular to the plane of radiation R (transversely), which prevents the biopsy needle 11 and cannula 12 from being displayed in a manner overlapping the springs, whereby it is possible to clearly display the biopsy needle 11 and cannula 12 on the image screen.

Figure 7:
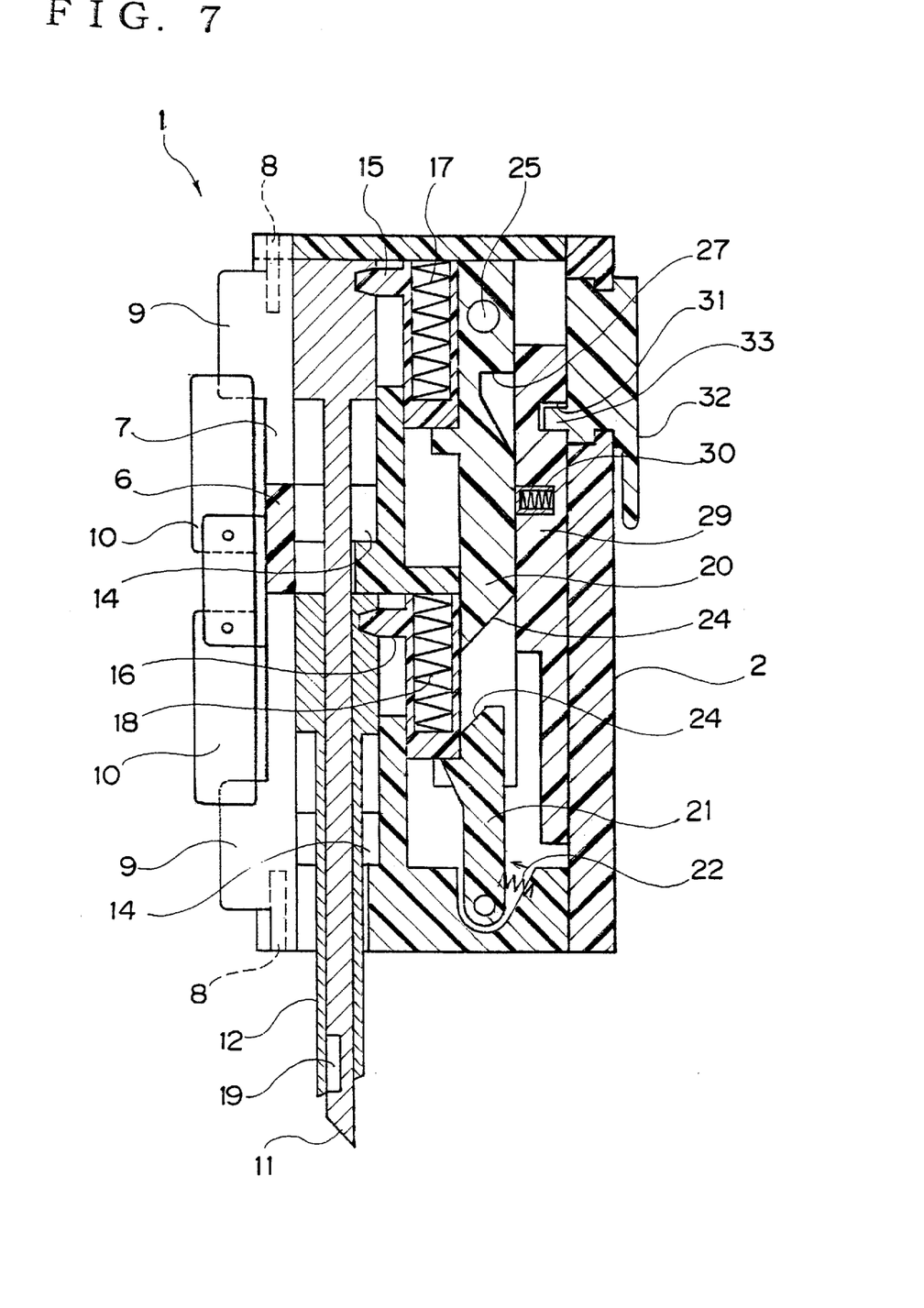
FIG. 7 is a cross-sectional view showing the biopsy device in a state in which the handle has been turned but a lock mechanism is not unlocked.

After effecting fine adjustment of the position and orientation of the biopsy needle 11, etc., next, the start button 26 of the housing 2 is depressed to push the biopsy needle 11 and the cannula 12 into any desired site of a human body. That is, when the handle 32 is turned downward to make the biopsy device 1 ready for biopsy operation, as shown in FIG. 7, the slider 29 is depressed downward by the projection 33 of the handle 32, and hence the latch 30 is detached downward from the latch recess 27 of the first stopper 20, whereby it becomes possible to move the first stopper 20 downward. In this state, however, the lock mechanism 25 is still engaged with the housing 2, thereby preventing the first stopper 20 from moving downward.

Figure 8:
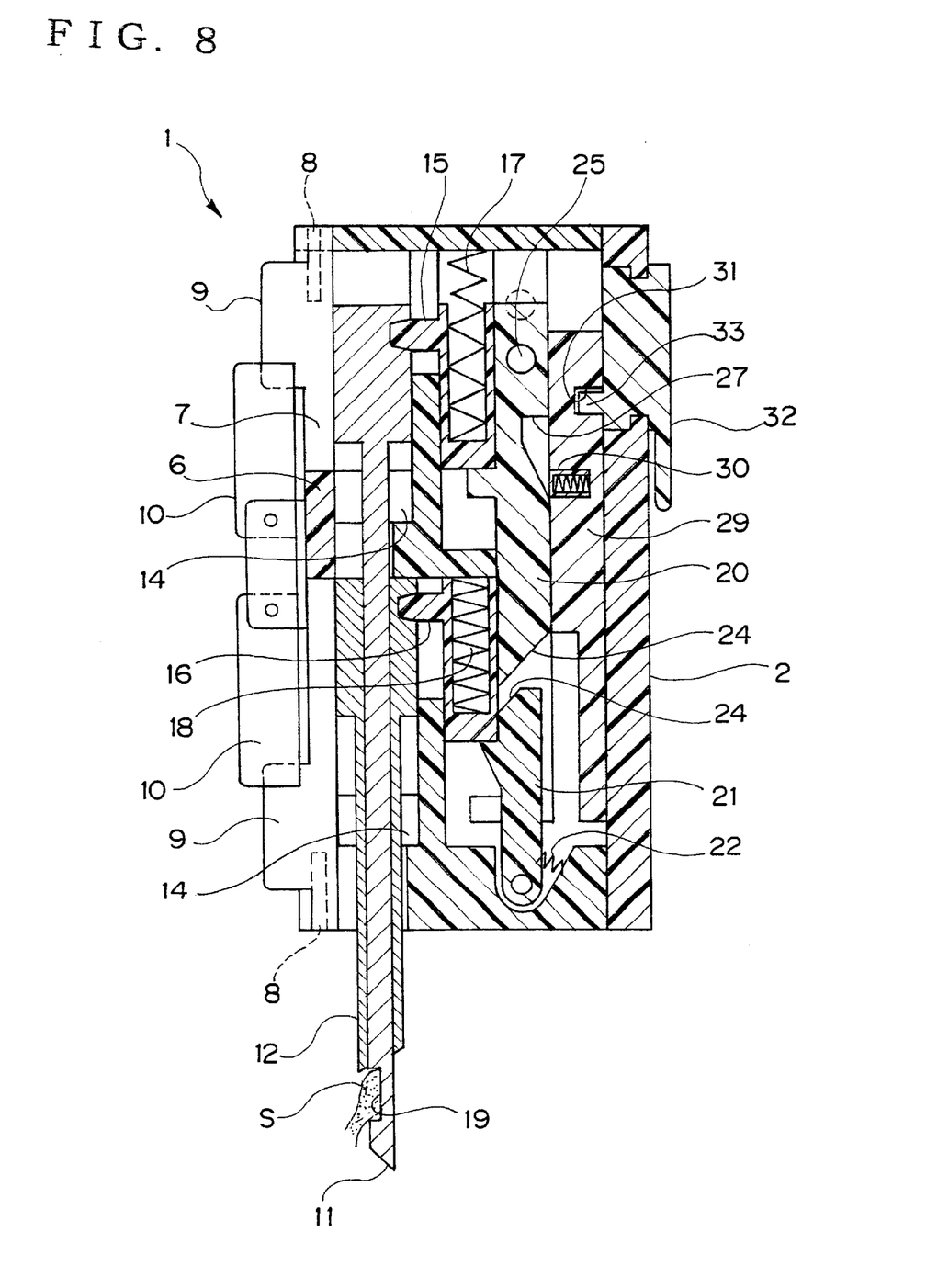
FIG. 8 is a cross-sectional view showing a state of the biopsy device at the moment that the handle has been turned and the lock mechanism is unlocked.

However, when the start button 26 is depressed, the lock mechanism 25 is caused to be disengaged from the housing 2, whereby the first stopper 20 is released and, as shown in FIG. 8, the first stopper 20 and the first hook 15 are moved downward by the urging force of the first metal spring 17 of the first hook 15 until the first hook 15 abuts the upper holder 14 of the lid 6. As the first hook 15 is moved downward, the biopsy needle 11 is protruded downward and inserted into the desired site of the human body. The distal end of the biopsy needle 11 is formed with the pocket 19 into which a sample tissue S of the desired site of the human body is received.

Figure 9:
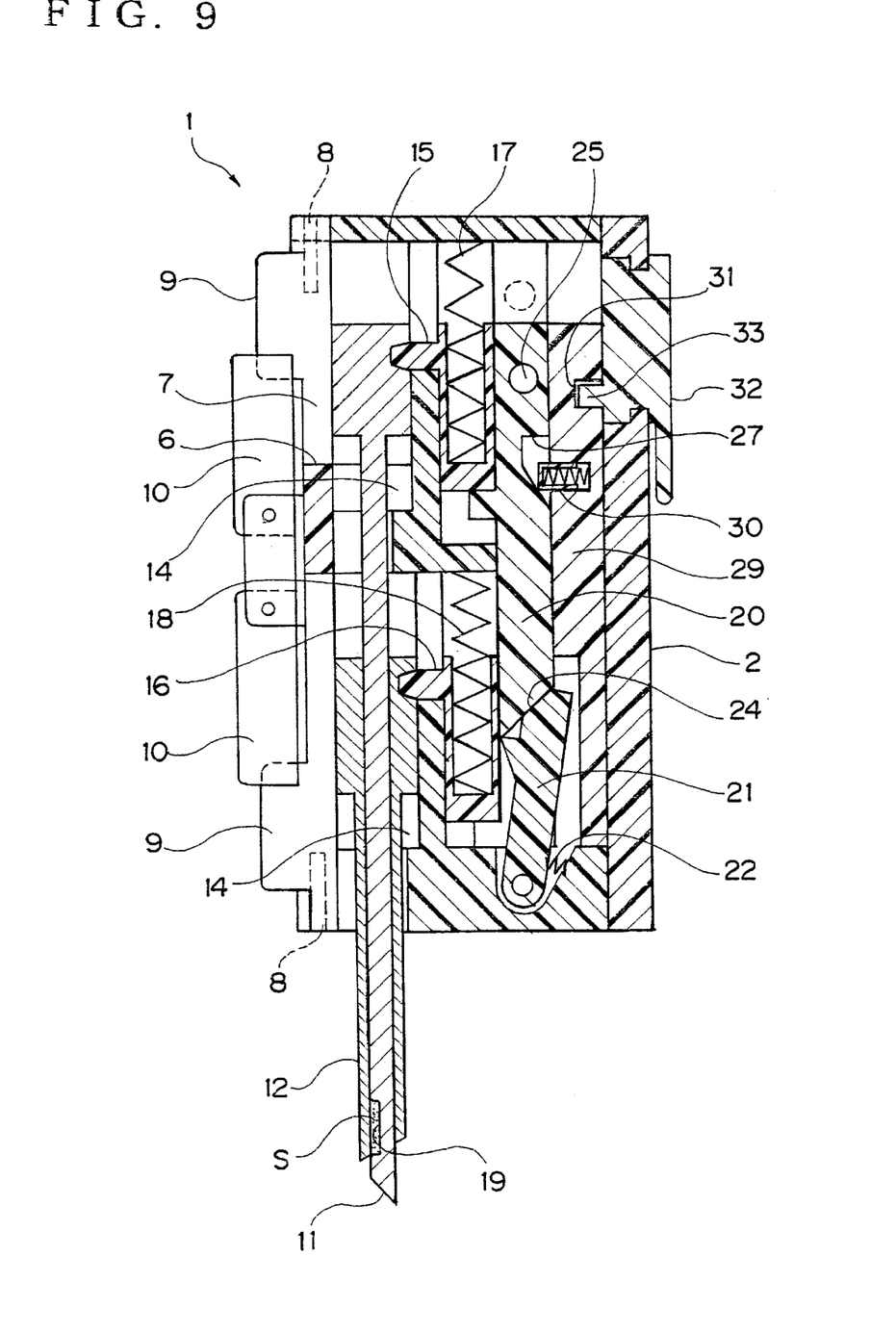
FIG. 9 is a cross-sectional view showing the biopsy device in a state in which the lock mechanism has been unlocked, and a first stopper moving downward abuts a second stopper to rotate the second stopper.
Figure 10:
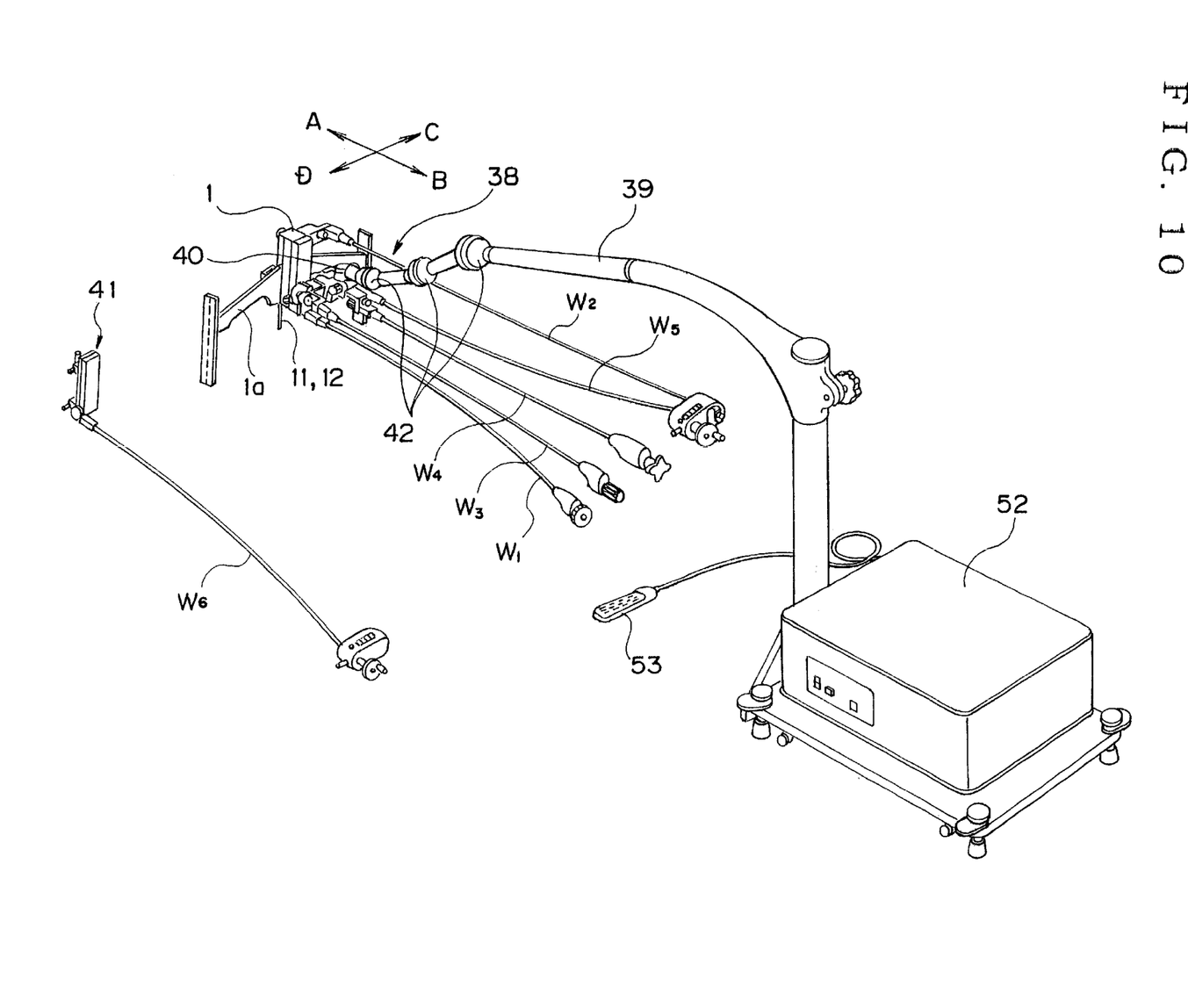
FIG. 10 is a perspective view of a remote control device according to a second embodiment of the invention.

Then, the first stopper 20 abuts the second stopper 21 arranged below the first stopper 20 to thereby rotate or pivotally move the second stopper 21, so that the second hook 16 is disengaged from the second stopper 21, which causes the cannula 12 to protrude downward until the same abuts the holder 14 of the lid 6 to thereby cut off the sample tissue in the pocket 19 and then close the pocket 19. By the above-mentioned procedure, the collection of the sample tissue S is completed. The biopsy needle 11 and the cannula 12 are withdrawn from the human body and the biopsy device 1 is removed from the same. The biopsy needle 11 and the cannula 12 can be easily removed from the housing 2 by removing the lid 6 from the housing 2.

FIGS. 10 to 14 show a second embodiment of the invention. According to the second embodiment, to prevent the operator from being exposed to doses of radiation, the biopsy device 1 shown in the first embodiment is held on a distal portion of an articulated arm 39 via a fine-adjustment mechanism 38 to thereby enable the biopsy device 1 to be remotely controlled. Reference numeral 41 designates an ethanol local injection device which can be attached to the fine-adjustment mechanism 38 instead of the biopsy device 1, and will be described hereinafter. Reference numeral 1a designates a positioning jig according to the second embodiment.

Figure 12:
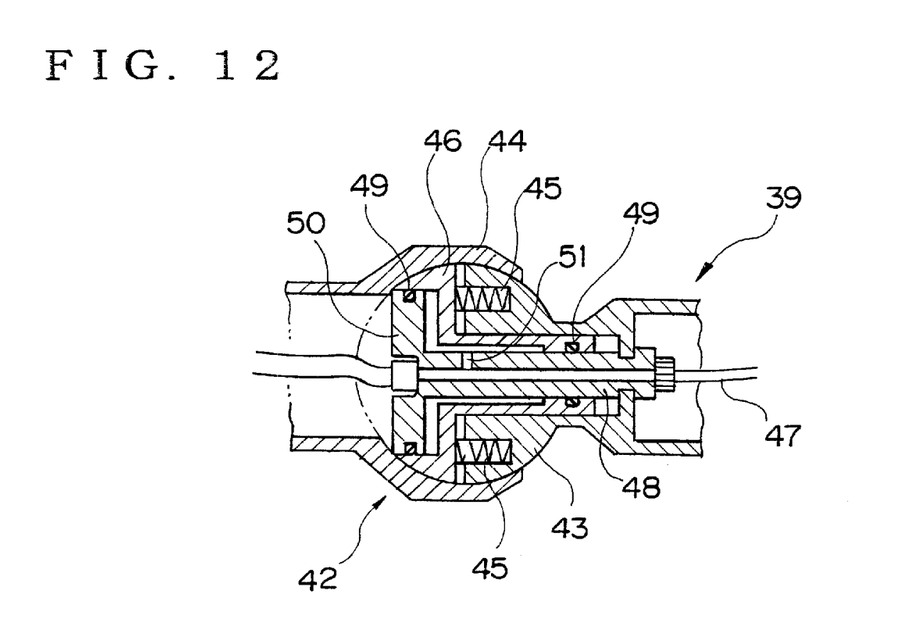
FIG. 12 is a cross-sectional view of a joint of an articulated arm of the remote control device according to the second embodiment.
Figure 13:
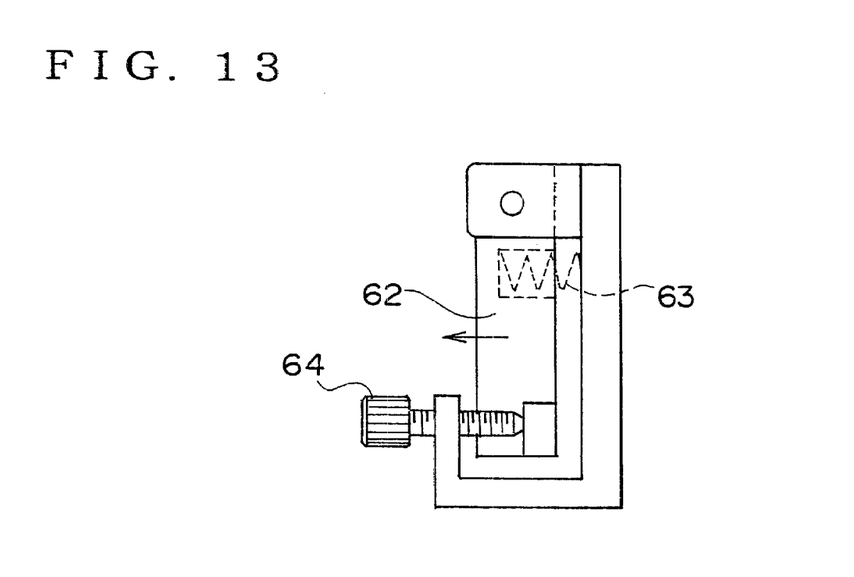
FIG. 13 is a side view of a pivotal member of the fine-adjustment mechanism of the remote control device.

The articulated arm 39 is constructed such that three joints 42 as articulations enable a distal end 40 of the articulated arm 39 to move freely. Each joint 42 has an internal bulb 43 and an external bulb 44, and the internal bulb 43 is provided with a clutch 46 pressed against an inner surface of the external bulb 44 by a pressure spring 45. An air hose 47 extends through each joint 42 and an air hose-connecting pipe 48 is provided at a central portion of the internal bulb 43. The connecting pipe 48 is formed at an end thereof with a flange 50 which is in air-tight contact with the clutch 46 via an O ring 49. At another end of the connecting pipe 48, another O ring 49 is provided which is in air-tight contact with the clutch 46. The connecting pipe 48 is formed with a hole 51 through which air can be forced in between the clutch 46 and the flange 50.

When air is forced in between the clutch 46 and the flange 50, the clutch 46 is moved by air pressure against the urging force of the pressure spring 45 to thereby disengage the clutch 46 from the inner surface of the external bulb 44 against which the clutch is pressed by the pressure spring 45. In this state, it is possible to freely move the joints 42. When the forcing of air is stopped, the clutch 46 is again pressed against the inner surface of the external bulb 44 by the pressure spring 45 to lock the joints 42. Thus, the joints 42 are mechanically locked by the pressure spring 45 which constantly applies its urging force to the clutch 46, so that even if air supply is interrupted by electric breakdown, the joints 42 are locked by the pressure spring 45, which is preferable from the viewpoint of safety. Air can be supplied or stopped by operating a foot switch 53 provided in a main block 52 of the articulated arm 39.

Figure 11:
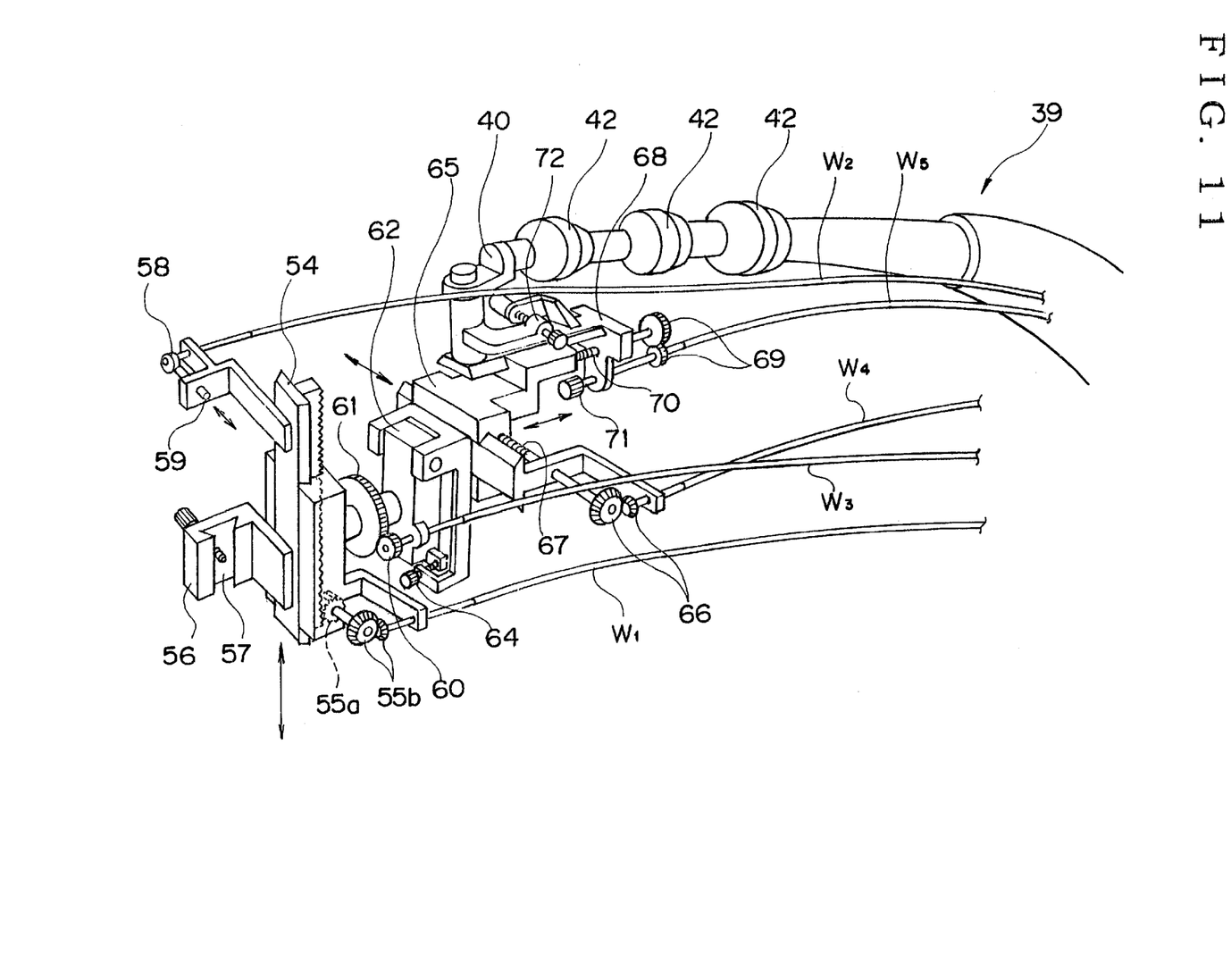
FIG. 11 is a perspective view of a fine-adjustment mechanism of the remote control device according to the second embodiment of the invention.

Next, the construction of the fine-adjustment mechanism 38 will be described with reference to FIG. 11. At a distal end of the fine-adjustment mechanism 38, a vertically moveable rack 54 is provided. The rack 54 is engaged with a gear 55a, and a pair of bevel gears 55b connected to the gear 55a are rotated by a wire cable W1 as "flexible transmission means" to thereby vertically move the rack 54.

The rack 54 is provided with an L-shaped frame 56 which is formed with a dovetail groove 57. The mounting block 28 formed on the right side of the housing 2 of the biopsy device 1 is inserted into the dovetail groove 57. An eccentric cam 58 is arranged on an upper portion of the rack 54, for being rotated by a wire cable W2. The eccentric cam 58 causes a pin 59 to protrude. The pin 59 is arranged at a location for pushing the start button 26 of the biopsy device 2.

A portion holding the rack 54 is rotated by a large diameter gear 61 engaging with a gear 60 of a wire cable W3. The large diameter gear 61 is mounted on a pivotal member 62 of which lower portion is pivotally moveable about a pivotal axis extending through an upper end of the member 62. The pivotal member 62 is urged forward by a spring 63 (see FIG. 13) and configured such that angular fine adjustment of the pivotal member 62 can be manually effected by operating a knob 64 having its end abutting against the pivotal member 62.

A portion supporting the pivotal member 62 is connected to a frame 65 by dovetail engagement in a manner movable rightward and leftward. The frame 65 is engaged with a screw 67 which is rotated by a pair of bevel gears 66 provided at an end of a wire cable W4 whereby the frame 65 can be moved in a rightward or leftward direction in accordance with rotation of the screw 67.

The frame 65 is connected to another frame 68 by dovetail engagement in a manner movable forward and backward. The frame 68 is engaged with a screw 70 which is rotated by a pair of gears 69 provided at an end of a wire cable W5 so as to move forward or backward in accordance with rotation of the screw 70. A knob 71 is arranged at an end of the wire cable W5 whereby fine adjustment in forward or backward position of the frame 68 can be manually effected. Further, the frame 68 can be rotated in a horizontal direction with respect to the distal end 40 of the articulated arms 39 by turning a screw 72.

As described above, according to the second embodiment, after setting the biopsy device 1 at an approximately suitable position by using the articulated arms 39, the operator can carry out a final positioning of the biopsy device 1 by remote control with the fine-adjustment mechanism 38 and operate the start button 26 of the biopsy device 1 by remote control with the wire cable W2, which prevents the operator from being exposed to doses of radiation.

Figure 14:
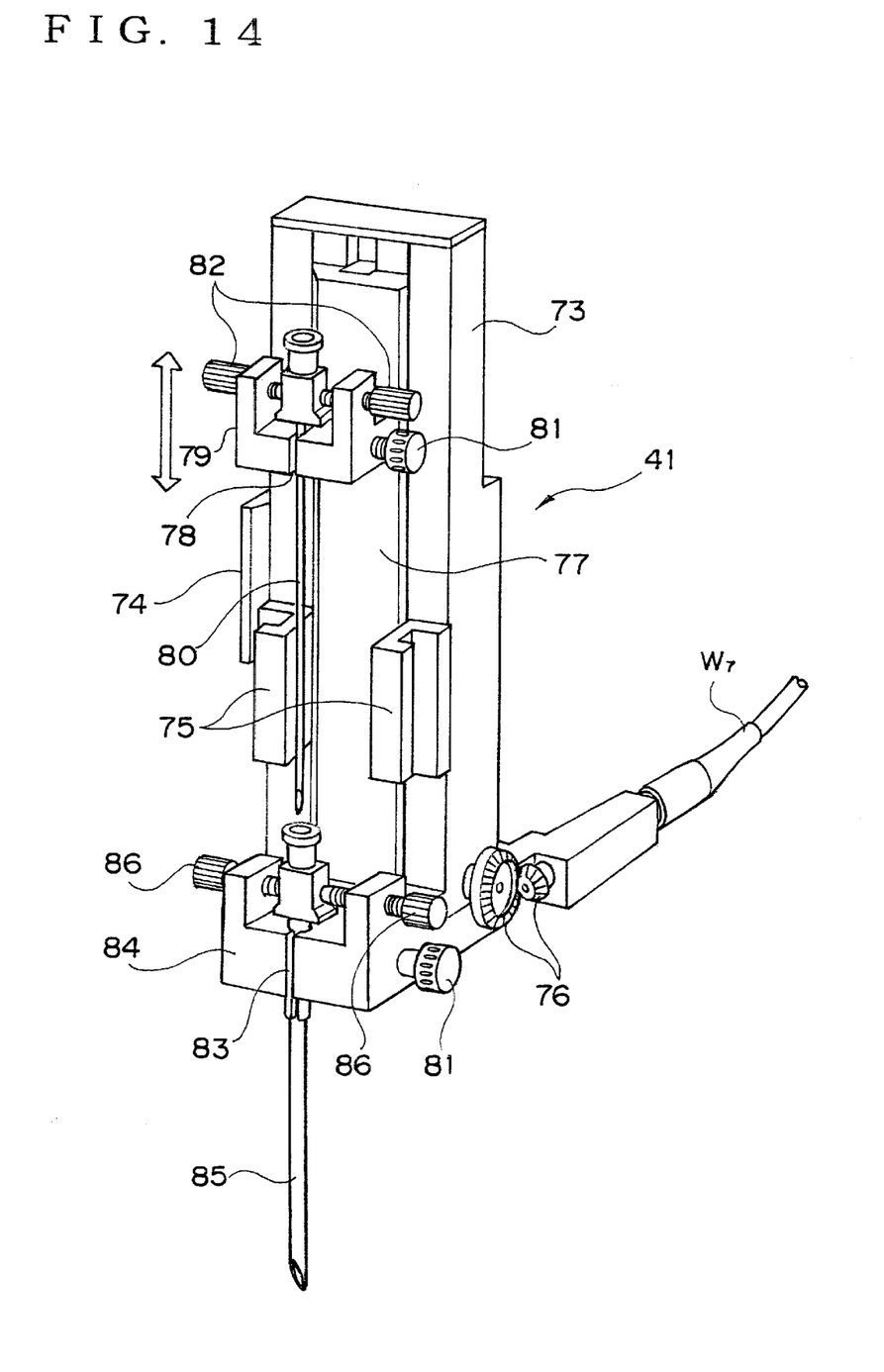
FIG. 14 is a perspective view of an ethanol local injection device mounted on the remote control device.

It should be noted that, as described above, instead of the biopsy device 1, the ethanol local injection device 41 can be mounted on the fine-adjustment mechanism 38. The mounting is effected by engaging a mounting block 74 formed on a side surface of a housing 73 of the ethanol local injection device 41 with the dovetail groove 58 of the fine-adjustment mechanism 38. Projections 75 are formed at vertically intermediate portions of the housing 73 of the ethanol local injection device 41, for engagement with the grooves 35 of the jig 34 of the first embodiment. The housing 73 is provided with a rack 77 which is vertically moved by a pair of bevel gears 76 attached to a wire cable W7. The wire cable W7 is different from that employed in the fine-adjustment mechanism 38.

The rack 77 is provided with a holder 79 which has a slot 78 for holding an ethanol injection needle 80 for injecting ethanol. The injection needle 80 can be supplied with ethanol through a tube, not shown. The holder 79 is formed with a crank knob 81 extending through the slot 78. The slot 78 can be narrowed by rotating the crank knob 81, whereby the injection needle 80 can be held in the slot 78. Further, the holder 79 is provided with a pair of screws 82 for holding an upper end of the injection needle 80 from opposite lateral sides to prevent the rotation of the injection needle 80.

A holder 84 having a slot 83 is also provided at a lower portion of the housing 73. The slot 83 holds a cannula 85. The holder 84 is also provided with a crank knob 81 and a pair of screws 86 for holding an upper end of the cannula 85 from opposite lateral sides.

The ethanol local injection device 41 constructed as above is positioned to a target site (tumor) of a human body under the guidance of the CT or the like and then the injection needle 80 guided by the cannula 85 is caused to be protruded downward to insert the same into the desired site of the human body to thereby inject ethanol from a pointed end of the injection needle 80. Thus, the target site (tumor) can be treated. The above ethanol treatment can be carried out by remote control, and which prevents the operator from being exposed to doses of radiation.

Figure 15:
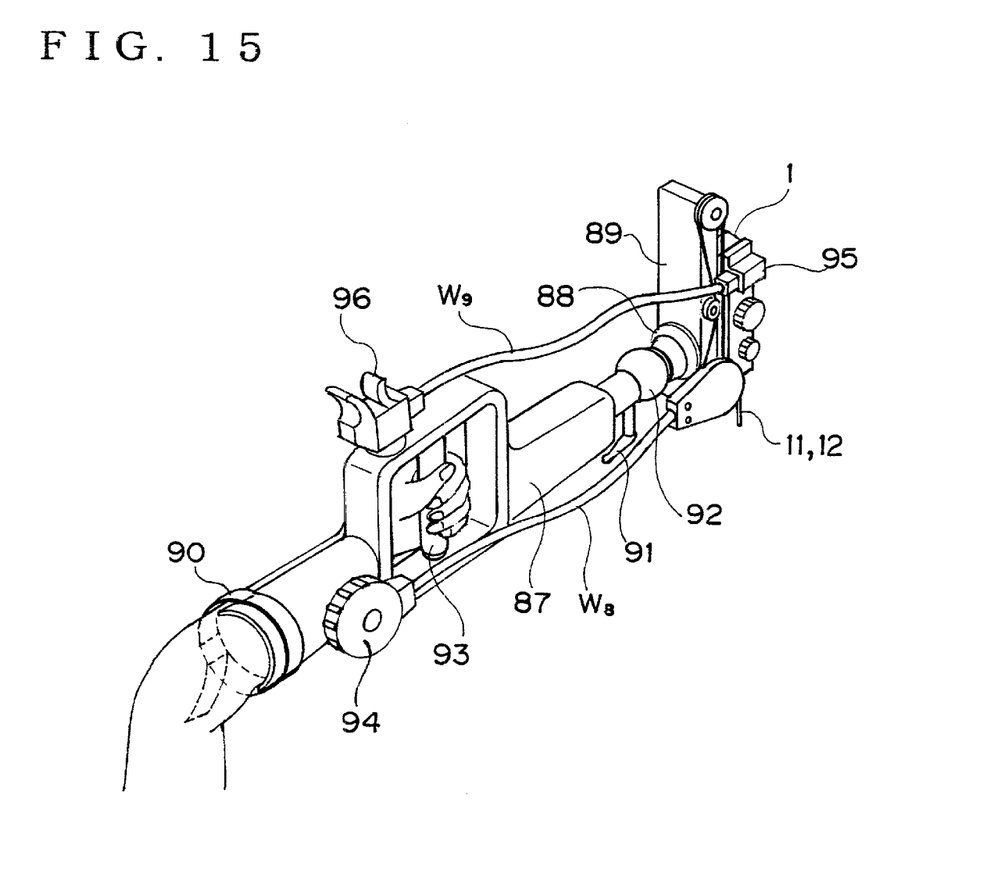
FIG. 15 is a perspective view of a remote control device according to a third embodiment of the invention.

FIG. 15 shows a third embodiment of the invention. The third embodiment shows a device which carries out a remote control to be carried out in a more simplified manner than the second embodiment. That is, the remote control device according to the third embodiment is mainly comprised of a holder 87 which can be attached to an arm of the operator, and a vertically-moving mechanism 89 as a "fine-adjustment mechanism" which is mounted on a distal end 88 of the holder 87.

The holder 87 can be attached to the operator's arm by using a belt 90. The distal end 88 is provided with a joint 92 which can be locked or unlocked by operating a lever 91. The angle of the distal end 88 can be freely changed by the joint 92. A grip 93 for the operator is provided at an intermediate portion of the holder 87.

The biopsy device 1 can be mounted on the vertically-moving mechanism 89. An operating force applied to the handle 94 by the operator is transmitted to the vertically-moving mechanism 89 via a wire cable W8, whereby the biopsy device 1 can be moved in the vertical direction by remote control. Further, the vertically-moving mechanism 89 is also provided with a trigger 95. The operating force of a switch lever 96 is transmitted to the trigger 95 via a wire cable W9, whereby it is possible to depress a start button, not shown, of the biopsy device 1 by remote control.

The remote control device according to the third embodiment is employed, similarly to the case of the second embodiment, to prevent the operator from being exposed to doses of radiation. Further, since the remote control device, according to the third embodiment, is used by attaching the same to the operator's arm, it can be operated more easily than the second embodiment.

In another preferred embodiment of the present invention, the biopsy needle and the cannula are positively spaced from the metal springs of the first hook and the second hook by a predetermined distance in a direction perpendicular to a plane of radiation and hence the biopsy needle and cannula are prevented from being displayed on the image screen in a manner overlapping the springs, whereby it is possible to reliably recognize the positions of the biopsy needle and the like.

In another preferred embodiment, the first stopper is permitted to move downward together with the first hook by unlocking the lock mechanism formed on a side of the first stopper between the first stopper and the housing, and when the first stopper has moved downward over a predetermined distance, it abuts a second stopper to thereby disengage the second stopper from the second hook, which allows the biopsy needle to protrude downward prior to protrusion of the cannula with a slight time lag.

In another preferred embodiment, the linear groove or linear ridge is aligned with the plane of radiation, whereby the biopsy needle and the cannula can be aligned with the plane of radiation.

In another preferred embodiment, the biopsy device is not held directly by hand but rather held on the distal end of the articulated arm to prevent the operator from being exposed to doses of radiation. Further, it is possible for the operator to operate the fine-adjustment mechanism for finely adjusting the position of the biopsy device and the lock mechanism of the biopsy device by flexible transmission means remote from the biopsy device. Furthermore, the above operation is executed mechanically, not electrically, thereby preventing generation of electrical noise.

In still another preferred embodiment, the biopsy device is not held directly by hand but rather held on the distal end of the holder and attachable to an operator's arm. This prevents the operator from being exposed to doses of radiation. It is possible to operate the fine-adjustment mechanism for finely adjusting the position of the biopsy device and the lock mechanism of the apparatus by flexible transmission means.

In yet another preferred embodiment, instead of the biopsy device, the ethanol local injection device is held on the distal end of the remote control device, whereby it is possible to effect ethanol local injection treatment under the guidance of the CT or the like.

What is claimed is:

1. A biopsy device, comprising:

a housing having a shape of a container, said housing having an opening on a first side thereof;

a cannula;

a biopsy needle, wherein said biopsy needle is inserted into said cannula, wherein said cannula and said biopsy needle are received within said housing such that said cannula and said biopsy needle are vertically movable within said housing;

a first hook, wherein said first hook is in engagement with said biopsy needle;

a first spring, wherein said first spring urges said biopsy needle downward;

a second hook, wherein said second hook is in engagement with said cannula; and a second spring, wherein said second spring urges said cannula downward;

wherein said first hook and said second hook are located within said housing, and further wherein said first hook releases said biopsy needle and said second hook releases said cannula causing said biopsy needle to protrude downward prior to said cannula protruding downward, wherein said biopsy needle is spaced apart from said first spring and said cannula is spaced apart from said second spring by a predetermined distance in a direction perpendicular to a plane of radiation, wherein said biopsy needle and said cannula are displayed on an image screen without overlapping said first spring and said second spring.

2. The biopsy device of claim 1, further comprising:

a first stopper associated with said first hook, wherein said first stopper inhibits a downward movement of said first hook;

a second stopper associated with said second hook, wherein second stopper inhibits a downward movement of said second hook; and a lock mechanism formed between said first stopper and said housing, wherein said first stopper is moveable downwardly together with said first hook by unlocking said lock mechanism, and further wherein said first stopper abuts said second stopper when said first stopper has moved downward over a predetermined distance to disengage said second stopper from said second hook.

3. The biopsy device of claim 2, wherein said housing further comprises:

at least one of a linear groove and a linear ridge formed on a side thereof at a location aligned with said biopsy needle and said cannula, wherein said biopsy needle and said cannula can be brought into alignment with a plane of radiation.

4. The biopsy device of claim 3, further comprising;

a remote control device for remotely controlling said biopsy device, wherein said remote control device further comprises:
  a fine-adjustment mechanism for finely adjusting a position of said biopsy device;
  an articulated arm having a distal end, wherein said biopsy device is held at said distal end of said articulated arm via said fine-adjustment mechanism; and
  a flexible transmission device via which said fine-adjustment mechanism and a lock mechanism of said biopsy device can be mechanically operated.

5. The biopsy device of claim 4, wherein said remote control device can at least one of provide remote control for and provide support for an enthanol local injection device.

6. The biopsy device of claim 3, further comprising:

a remote control device for remotely controlling said biopsy device, wherein said remote control device further comprises:
  a fine-adjustment mechanism for finely adjusting a position of said biopsy device;
  a holder attachable to an operator's arm, wherein said biopsy device can be held at a distal end of said holder via said fine-adjustment mechanism; and
  a flexible transmission device via which said fine-adjustment mechanism and a lock mechanism of said biopsy device can be mechanically operated.

7. The biopsy device of claim 6, wherein said remote control device can at least one of provide remote control for and provide support for an enthanol local injection device.

8. The biopsy device of claim 2, further comprising;

a remote control device for remotely controlling said biopsy device, wherein said remote control device further comprises:
  a fine-adjustment mechanism for finely adjusting a position of said biopsy device;
  an articulated arm having a distal end, wherein said biopsy device is held at said distal end of said articulated arm via said fine-adjustment mechanism; and
  a flexible transmission device via which said fine-adjustment mechanism and a lock mechanism of said biopsy device can be mechanically operated.

9. The biopsy device of claim 8, wherein said remote control device can at least one of provide remote control for and provide support for an enthanol local injection device.

10. The biopsy device of claim 2, further comprising:

a remote control device for remotely controlling said biopsy device, wherein said remote control device further comprises:
  a fine-adjustment mechanism for finely adjusting a position of said biopsy device;
  a holder attachable to an operator's arm, wherein said biopsy device can be held at a distal end of said holder via said fine-adjustment mechanism; and
  a flexible transmission device via which said fine-adjustment mechanism and a lock mechanism of said biopsy device can be mechanically operated.

11. The biopsy device of claim 10, wherein said remote control device can at least one of provide remote control for and provide support for an enthanol local injection device.

12. The biopsy device of claim 1, wherein said housing further comprises:

at least one of a linear groove and a linear ridge formed on a side thereof at a location aligned with said biopsy needle and said cannula, wherein said biopsy needle and said cannula con be brought into alignment with a plane of radiation.

13. The biopsy device of claim 12, further comprising;

a remote control device for remotely controlling said biopsy device, wherein said remote control device further comprises:
  a fine-adjustment mechanism for finely adjusting a position of said biopsy device;
  an articulated arm having a distal end, wherein said biopsy device is held at said distal end of said articulated arm via said fine-adjustment mechanism; and
  a flexible transmission device via which said fine-adjustment mechanism and a lock mechanism of said biopsy device can be mechanically operated.

14. The biopsy device of claim 13, wherein said remote control device can at least one of provide remote control for and provide support for an enthanol local injection device.

15. The biopsy device of claim 12, further comprising:

a remote control device for remotely controlling said biopsy device, wherein said remote control device further comprises:
  a fine-adjustment mechanism for finely adjusting a position of said biopsy device;
  a holder attachable to an operator's arm, wherein said biopsy device can be held at a distal end of said holder via said fine-adjustment mechanism; and
  a flexible transmission device via which said fine-adjustment mechanism and a lock mechanism of said biopsy device can be mechanically operated.

16. The biopsy device of claim 15, wherein said remote control device can at least one of provide remote control for and provide support for an enthanol local injection device.

17. The biopsy device of claim 1, further comprising;

a remote control device for remotely controlling said biopsy device, wherein said remote control device further comprises:
  a fine-adjustment mechanism for finely adjusting a position of said biopsy device;
  an articulated arm having a distal end, wherein said biopsy device is held at said distal end of said articulated arm via said fine-adjustment mechanism; and
  a flexible transmission device via which said fine-adjustment mechanism and a lock mechanism of said biopsy device can be mechanically operated.

18. The biopsy device of claim 17, wherein said remote control device can at least one of provide remote control for and provide support for an enthanol local injection device.

19. The biopsy device of claim 1, further comprising:
a remote control device for remotely controlling said biopsy device, wherein said remote control device further comprises:
a fine-adjustment mechanism for finely adjusting a position of said biopsy device;
a holder attachable to an operator's arm, wherein said biopsy device can be held at a distal end of said holder via said fine-adjustment mechanism; and
a flexible transmission device via which said fine-adjustment mechanism and a lock mechanism of said biopsy device can be mechanically operated.

20. The biopsy device of claim 19, wherein said remote control device can at least one of provide remote control for and provide support for an enthanol local injection device.

21. A combination, comprising:
at least one of a magnetic resonance imaging device and a CT device; and
a biopsy device, wherein said biopsy device further comprises:
a housing having a shape of a container, said housing having an opening on a first side thereof;
a cannula;
a biopsy needle, wherein said biopsy needle is inserted into said cannula, wherein said cannula and said biopsy needle are received within said housing such that said cannula and said biopsy needle are vertically movable within said housing;
a first hook, wherein said first hook is in engagement with said biopsy needle;
a first spring, wherein said first spring urges said biopsy needle downward;
a second hook, wherein said second hook is in engagement with said cannula; and
a second spring, wherein said second spring urges said cannula downward;
wherein said first hook and said second hook are located within said housing, and further wherein said first hook releases said biopsy needle and said second hook releases said cannula causing said biopsy needle to protrude downward prior to said cannula protruding downward,
wherein said biopsy needle is spaced apart from said first spring and said cannula is spaced apart from said second spring by a predetermined distance in a direction perpendicular to a plane of radiation, wherein said biopsy needle and said cannula are displayed on an image screen without overlapping said first spring and said second spring.

22. The combination of claim 21, wherein said biopsy device further comprises:
a first stopper associated with said first hook, wherein said first stopper inhibits a downward movement of said first hook;
a second stopper associated with said second hook, wherein second stopper inhibits a downward movement of said second hook; and
a lock mechanism formed between said first stopper and said housing, wherein said first stopper is moveable downwardly together with said first hook by unlocking said lock mechanism, and further wherein said first stopper abuts said second stopper when said first stopper has moved downward over a predetermined distance to disengage said second stopper from said second hook.

23. The combination of claim 21, wherein said biopsy device further comprises:
at least one of a linear groove and a linear ridge formed on a side thereof at a location aligned with said biopsy needle and said cannula, wherein said biopsy needle and said cannula can be brought into alignment with a plane of radiation.

24. The combination of claim 21, wherein said biopsy device further comprises:
a remote control device for remotely controlling said biopsy device, wherein said remote control device further comprises:
a fine-adjustment mechanism for finely adjusting a position of said biopsy device;
an articulated arm having a distal end, wherein said biopsy device is held at said distal end of said articulated arm via said fine-adjustment mechanism; and
a flexible transmission device via which said fine-adjustment mechanism and a lock mechanism of said biopsy device can be mechanically operated.

25. The combination of claim 24, wherein said remote control device can at least one of provide remote control for and provide support for an enthanol local injection device.

26. The combination of claim 21, wherein said biopsy device further comprises:
a remote control device for remotely controlling said biopsy device, wherein said remote control device further comprises:
a fine-adjustment mechanism for finely adjusting a position of said biopsy device;
a holder attachable to an operator's arm, wherein said biopsy device can be held at a distal end of said holder via said fine-adjustment mechanism; and
a flexible transmission device via which said fine-adjustment mechanism and a lock mechanism of said biopsy device can be mechanically operated.

27. The combination of claim 26, wherein said remote control device can at least one of provide remote control for and provide support for an enthanol local injection device.

* * * * *